United States Patent
Hinago et al.

[11] Patent Number: 6,063,728
[45] Date of Patent: May 16, 2000

[54] AMMOXIDATION CATALYST FOR USE IN PRODUCING ACRYLONITRILE OR METHACRYLONITRILE FROM PROPANE OR ISOBUTANE BY AMMOXIDATION

[75] Inventors: Hidenori Hinago, Kurashiki; Satoru Komada, Yokohama, both of Japan

[73] Assignee: Asahi Kasei Kogyo Kabushiki Kaisha, Osaka, Japan

[21] Appl. No.: 09/129,414

[22] Filed: Aug. 5, 1998

[30] Foreign Application Priority Data

Aug. 5, 1997 [JP] Japan ................................. 9-222041
Dec. 24, 1997 [JP] Japan ................................. 9-355496

[51] Int. Cl.$^7$ ............................ B01J 23/00; B01J 23/40; B01J 23/58; B01J 23/02; C07C 253/00

[52] U.S. Cl. ........................ 502/300; 502/308; 502/309; 502/311; 502/312; 502/313; 502/315; 502/316; 502/317; 502/321; 502/324; 502/325; 502/326; 502/327; 502/328; 502/330; 502/332; 502/333; 502/337; 502/338; 502/339; 502/340; 502/341; 502/344; 502/353; 558/325; 558/318; 558/319; 558/321; 558/322; 558/323; 558/324

[58] Field of Search ............................ 502/202, 204–213, 502/215, 300, 302, 306, 308–317, 321–328, 332–341, 330, 344, 347–355; 558/318, 319, 321–325

[56] References Cited

U.S. PATENT DOCUMENTS

| | | | |
|---|---|---|---|
| 4,760,159 | 7/1988 | Suresh et al. | 558/319 |
| 4,797,381 | 1/1989 | Bartek et al. | 502/202 |
| 5,049,692 | 9/1991 | Hatano et al. | 558/319 |
| 5,134,105 | 7/1992 | Paparizos et al. | 502/212 |
| 5,231,214 | 7/1993 | Ushikubo et al. | 558/319 |
| 5,281,745 | 1/1994 | Ushikubo et al. | 558/319 |
| 5,422,328 | 6/1995 | Ushikubo et al. | 502/312 |
| 5,472,925 | 12/1995 | Ushikubo et al. | 502/319 |
| 5,534,650 | 7/1996 | Ushikubo et al. | 558/319 |
| 5,808,143 | 9/1998 | Karrer et al. | 502/352 |

FOREIGN PATENT DOCUMENTS

| | | |
|---|---|---|
| 0 767 164 A1 | 4/1997 | European Pat. Off. |
| 5-213848A | 8/1993 | Japan |
| 6-227819A | 8/1994 | Japan |
| 7-144132A | 6/1995 | Japan |
| 7-232071A | 9/1995 | Japan |
| 8-57319A | 3/1996 | Japan |
| 8-141401A | 6/1996 | Japan |

OTHER PUBLICATIONS

Centi et al. ; V–Sb–oxide catalysts for the ammoxidation of propane, Applied Catalysis, p144–p172, 1997 Month not available.

*Primary Examiner*—Mark L. Bell
*Assistant Examiner*—Patricia L. Hailey
*Attorney, Agent, or Firm*—Pennie & Edmonds LLP

[57] ABSTRACT

An ammoxidation catalyst comprising a compound oxide of Mo, V, Nb, and at least one element selected from the group consisting of Te and Sb, wherein the compound catalyst exhibits an X-ray diffraction pattern satisfying the following relationship:

$$0.40 \leq R \leq 0.75$$

wherein R represents the intensity ratio defined by the following formula:

$$R = P_1/(P_1+P_2)$$

wherein $P_1$ and $P_2$ represent the intensities of peak 1 and peak 2 appearing at diffraction angles (2θ) of 27.3±0.3° and 28.2±0.3°, respectively.

By the use of the ammoxidation catalyst of the present invention, not only can acrylonitrile or methacrylonitrile be produced in high yield, but also oxidative decomposition of ammonia feedstock into nitrogen can be effectively suppressed, thereby enabling an improved utilization of ammonia as a feedstock.

4 Claims, 8 Drawing Sheets

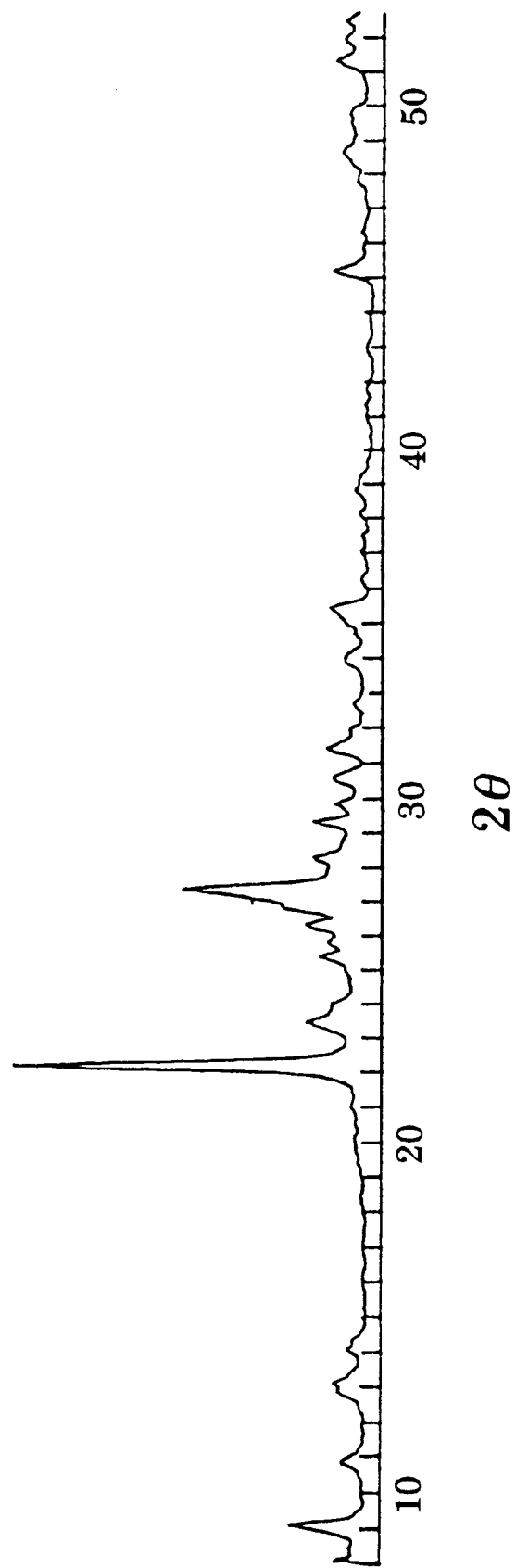

US 6,063,728

AMMOXIDATION CATALYST FOR USE IN PRODUCING ACRYLONITRILE OR METHACRYLONITRILE FROM PROPANE OR ISOBUTANE BY AMMOXIDATION

BACKGROUND OF THE INVENTION

1. Field of the Invention

The present invention relates to an ammoxidation catalyst for use in producing acrylonitrile or methacrylonitrile from propane or isobutane by ammoxidation in the gaseous phase. More particularly, the present invention is concerned with an ammoxidation catalyst comprising a compound oxide which contains specific component elements in specific atomic ratios and which exhibits an X-ray diffraction pattern wherein the intensities of two peaks respectively appearing at diffraction angles (2θ) of 27.3±0.3° and 28.2±0.3° have a specific relationship to each other. By the use of the ammoxidation catalyst of the present invention, not only can acrylonitrile or methacrylonitrile be produced in high yield, but also oxidative decomposition of ammonia feedstock into nitrogen can be effectively suppressed, thereby enabling an improved utilization of ammonia as a feedstock. The present invention is also concerned with a process for producing acrylonitrile or methacrylonitrile by using such an excellent ammoxidation catalyst.

2. Prior Art

There has been a well-known process for producing acrylonitrile or methacrylonitrile by ammoxidation of propylene or isobutylene. Recently, as a substitute for such a process using propylene or isobutylene, attention has been attracted to a process for producing acrylonitrile or methacrylonitrile by gaseous phase catalytic ammoxidation of propane or isobutane, i.e., by gaseous phase catalytic reaction of propane or isobutane with ammonia and molecular oxygen. Further, a number of proposals have been made with respect to catalysts for use in the ammoxidation of propane or isobutane.

For example, as a catalyst for use in producing acrylonitrile or methacrylonitrile by ammoxidation of propane or isobutane, oxide catalysts containing molybdenum, vanadium, niobium and tellurium are known. Such oxide catalysts are disclosed in U.S. Pat. No. 5,049,692, U.S. Pat. No. 5,231,214, U.S. Pat. No. 5,281,745, U.S. Pat. No. 5,422,328, Unexamined Japanese Patent Application Laid-Open Specification No. 6-227819, Unexamined Japanese Patent Application Laid-Open Specification No. 7-144132, Unexamined Japanese Patent Application Laid-Open Specification No. 7-232071, Unexamined Japanese Patent Application Laid-Open Specification No. 8-57319 and Unexamined Japanese Patent Application Laid-Open Specification No. 8-141401.

Further, oxide catalysts containing molybdenum, vanadium, antimony and niobium are disclosed in European Patent Application Publication No. 767 164 A1 and Unexamined Japanese Patent Application Laid-Open Specification No. 5-213848.

In addition, oxide catalysts containing vanadium and antimony are disclosed in U.S. Pat. No. 4,760,159 and U.S. Pat. No. 4,797,381.

Among the above-mentioned prior art documents, each of U.S. Pat. No. 5,281,745 and U.S. Pat. No. 5,422,328 discloses a crystalline metal oxide catalyst exhibiting an X-ray diffraction pattern having peaks at diffraction angles (2θ) of 22.1±0.3°, 28.2±0.3°, 36.2±0.3°, 45.2±0.3° and 50.0±0.3°, respectively; Unexamined Japanese Patent Application Laid-Open Specification No. 6-227819 discloses a crystalline metal oxide catalyst exhibiting an X-ray diffraction pattern having peaks at diffraction angles (2θ) of 22.1±0.5°, 28.2±0.5°, 36.2±0.5°, 45.2±0.5° and 50.0±0.5°, respectively; and Unexamined Japanese Patent Application Laid-Open Specification No. 7-232071 discloses a crystalline metal oxide catalyst exhibiting an X-ray diffraction pattern having peaks at diffraction angles (2θ) of 9.0±0.3°, 22.1±0.3°, 27.3±0.3°, 29.2±0.3° and 35.4±0.3°, respectively. However, in any of these prior art documents, there is no description about the intensity ratio of peaks appearing at diffraction angles (2θ) of 27.3±0.3° and 28.2±0.3°, respectively.

The oxide catalysts described in these prior art documents are disadvantageous in that none of them exhibit a satisfactorily high yield of acrylonitrile or methacrylonitrile in the ammoxidation of propane or isobutane.

*Applied Catalysis A General* (vol. 157, pp. 143–172, 1997) describes that, during the course of the ammoxidation of propane, ammonia, which is one of the gaseous feedstocks for the ammoxidation is converted not only to acrylonitrile as a desired product, but also inevitably to by-products, such as acetonitrile and hydrocyanic acid, and, is oxidatively decomposed into nitrogen. The conventional catalysts for use in the ammoxidation of propane or isobutane pose a problem in that, during the ammoxidation, decomposition of ammonia into nitrogen occurs to a high extent. Therefore, it is desired to develop an improved catalyst having an advantage in that the decomposition of ammonia during the ammoxidation can be suppressed, thereby enabling an efficient utilization of the feedstock ammonia for the ammoxidation of propane or isobutane.

On the other hand, U.S. Pat. No. 5,534,650 discloses a method for performing an ammoxidation of an alkane in which gaseous ammonia is fed into a reactor from a plurality of ammonia inlets provided therein so that the fed ammonia is efficiently utilized for the ammoxidation reaction. However, this method is disadvantageous not only in that extensive operations are required due to the use of complicated equipment, but also in that a satisfactory effect for suppressing the ammonia decomposition cannot be obtained.

SUMMARY OF THE INVENTION

In this situation, the present inventors have conducted extensive and intensive studies with a view toward developing an improved catalyst for use in producing acrylonitrile or methacrylonitrile from propane or isobutane by ammoxidation in the gaseous phase, which enables the ammoxidation in which not only can a high yield of acrylonitrile or methacrylonitrile be achieved, but also a decomposition of feedstock ammonia into nitrogen can be effectively suppressed, thereby enabling an improved utilization of feedstock ammonia. As a result, it has unexpectedly been found that the above objective can be achieved by an ammoxidation catalyst comprising a compound oxide which contains specific component elements in specific atomic ratios and which exhibits an X-ray diffraction pattern satisfying the following relationship:

$$0.40 \leq R \leq 0.75$$

wherein R represents the intensity ratio defined by the following formula:

$$R = P_1/(P_1 + P_2)$$

wherein $P_1$ and $P_2$ represent the intensities of peak 1 and peak 2 appearing at diffraction angles (2θ) of 27.3±0.3° and 28.2±0.3°, respectively.

The present invention has been completed, based on the above novel finding.

Accordingly, it is an object of the present invention to provide an ammoxidation catalyst for use in producing acrylonitrile or methacrylonitrile from propane or isobutane by ammoxidation in the gaseous phase, which is advantageous not only in that acrylonitrile or methacrylonitrile can be produced in high yield, but also in that an oxidative decomposition of feedstock ammonia into nitrogen can be effectively suppressed, thereby enabling an improved utilization of feedstock ammonia.

It is another object of the present invention to provide a process for producing acrylonitrile or methacrylonitrile from propane or isobutane by ammoxidation using such an excellent catalyst.

The foregoing and other objects, features and advantages of the present invention will be apparent to those skilled in the art from the following detailed description taken in connection with the accompanying drawings and the appended claims.

BRIEF DESCRIPTION OF DRAWINGS

In the drawings:

FIG. 8 is an XRD pattern of the ammoxidation catalyst obtained in Comparative Example 12.

Figure 1:
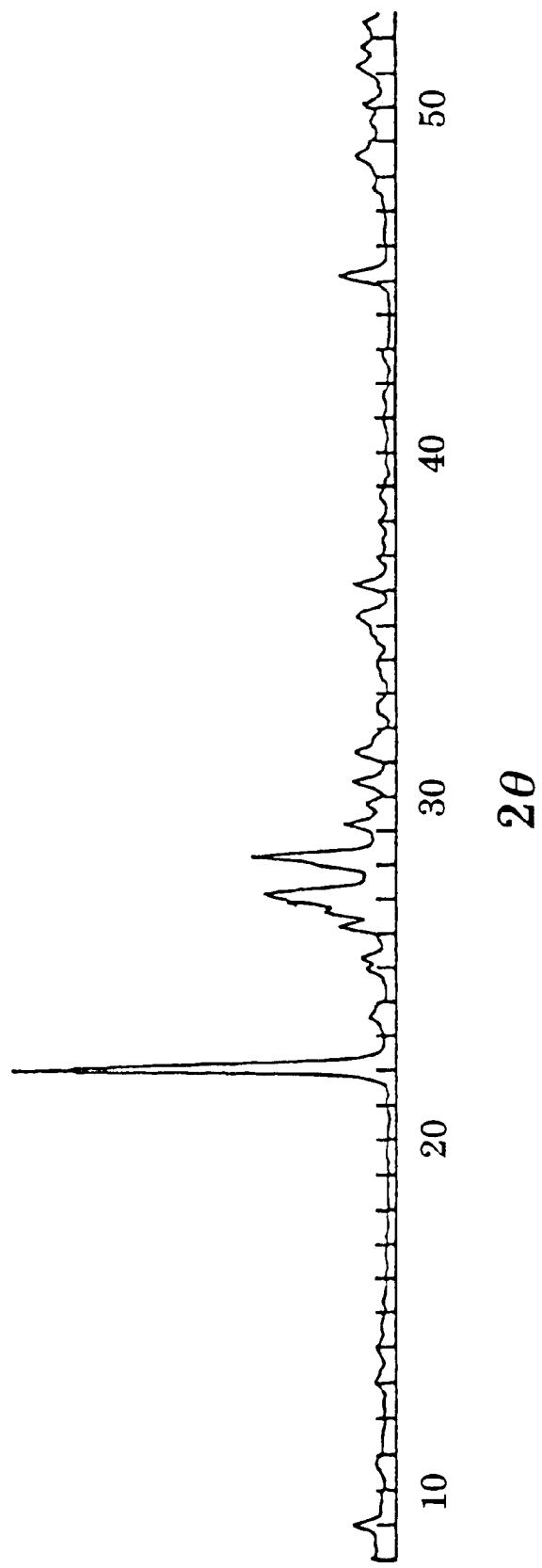
FIG. 1 is an X-ray diffraction pattern (hereinafter, frequently referred to simply as "XRD pattern") of the ammoxidation catalyst obtained in Example 1.

DESCRIPTION OF REFERENCE NUMERALS $A_1$: Apex of peak 1

$A_2$: Apex of peak 2

$B_1$: Point at which the curved line of the XRD pattern exhibits a minimum value, as viewed along the intensity axis vertical to the 2θ-axis, in the range of 26.4±0.3° in terms of the diffraction angle (2θ)

$B_2$: Point at which the curved line of the XRD pattern exhibits a minimum value, as viewed along the intensity axis vertical to the 2θ-axis, in the range of 27.7±0.3° in terms of the diffraction angle (2θ)

$B_3$: Point at which the curved line of the XRD pattern exhibits a minimum value, as viewed along the intensity axis vertical to the 2θ-axis, in the range of 28.8±0.3° in terms of the diffraction angle (2θ)

$C_1$: Point at which a straight line drawn downwardly from peak apex $A_1$ vertically to the 2θ-axis intersects with a straight line connecting points $B_1$ and $B_2$ $C_2$: Point at which a straight line drawn downwardly from peak apex $A_2$ vertically to the 2θ-axis intersects with a straight line connecting points $B_2$ and $B_3$

DETAILED DESCRIPTION OF THE INVENTION

In one aspect of the present invention, there is provided an ammoxidation catalyst for use in producing acrylonitrile or methacrylonitrile from propane or isobutane by ammoxidation in the gaseous phase, comprising a compound oxide represented by the following formula (1):

$$Mo_{0.1}V_pX_qNb_rZ_sO_n \quad (1)$$

wherein:

X is at least one element selected from the group consisting of tellurium and antimony;

Z is at least one element selected from the group consisting of tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals; and p, q, r, s and n are, respectively, the atomic ratios of vanadium, X, niobium, Z and oxygen, relative to molybdenum, wherein $0.1 \leq p \leq 0.6$;

$0.01 \leq q \leq 0.6$;

$0.01 \leq r \leq 0.6$;

$0 \leq s \leq 1$;

and n is a number determined by the valence requirements of the other elements present, the compound oxide exhibiting an X-ray diffraction pattern satisfying the following relationship (2):

$$0.40 \leq R \leq 0.75 \quad (2)$$

wherein R represents the intensity ratio defined by the following formula (3):

$$R = P_1/(P_1 + P_2) \quad (3)$$

wherein $P_1$ and $P_2$ represent the intensities of peak 1 and peak 2 appearing at diffraction angles (2θ) of 27.3±0.3° and 28.2±0.3°, respectively.

In another aspect of the present invention, there is provided a process for producing acrylonitrile or methacrylonitrile, which comprises reacting propane or isobutane with ammonia and molecular oxygen in the gaseous phase in the presence of the catalyst defined above.

For an easy understanding of the present invention, the essential features and various preferred embodiments of the present invention are enumerated below.

1. An ammoxidation catalyst for use in producing acrylonitrile or methacrylonitrile from propane or isobutane by ammoxidation in the gaseous phase, comprising a compound oxide represented by the following formula (1):

$$Mo_{1.0}V_pX_qNb_rZ_sO_n \quad (1)$$

wherein:

X is at least one element selected from the group consisting of tellurium and antimony;

Z is at least one element selected from the group consisting of tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals; and p, q, r, s and n are, respectively, the atomic ratios of vanadium, X, niobium, Z and oxygen, relative to molybdenum, wherein $$0.1 \leq p \leq 0.6;$$

$$0.01 \leq q \leq 0.6;$$

$$0.01 \leq r \leq 0.6;$$

$$0 \leq s \leq 1;$$

and n is a number determined by the valence requirements of the other elements present, the compound oxide exhibiting an X-ray diffraction pattern satisfying the following relationship (2):

$$0.40 \leq R \leq 0.75 \qquad (2)$$

wherein R represents the intensity ratio defined by the following formula (3):

$$R = P_1/(P_1 + P_2) \qquad (3)$$

wherein $P_1$ and $P_2$ represent the intensities of peak 1 and peak 2 appearing at diffraction angles (2θ) of 27.3±0.3° and 28.2±0.3°, respectively.

2. The catalyst according to item 1 above, wherein R in relationship (2) satisfies the following relationship:

$$0.43 \leq R \leq 0.70.$$

3. The catalyst according to item 1 or 2 above, which further comprises a silica carrier having supported thereon the compound oxide, wherein the silica carrier is present in an amount of from 20 to 60% by weight, based on the total weight of the compound oxide and the silica carrier.

4. A process for producing acrylonitrile or methacrylonitrile, which comprises reacting propane or isobutane with ammonia and molecular oxygen in the gaseous phase in the presence of the catalyst of item 1 above.

5. The process according to item 4 above, wherein R in relationship (2) satisfies the following relationship:

$$0.43 \leq R \leq 0.70.$$

6. The process according to item 4 or 5 above, wherein the catalyst further comprises a silica carrier having supported thereon the compound oxide, wherein the silica carrier is present in an amount of from 20 to 60% by weight, based on the total weight of the compound oxide and the silica carrier.

Hereinbelow, the present invention will be described in more detail.

The ammoxidation catalyst of the present invention has a characteristic feature in that it comprises a compound oxide represented by the following formula (1):

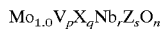
$$Mo_{1.0}V_pX_qNb_rZ_sO_n \qquad (1)$$

wherein:

X is at least one element selected from the group consisting of tellurium and antimony;

Z is at least one element selected from the group consisting of tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals; and p, q, r, s and n are, respectively, the atomic ratios of vanadium, X, niobium, Z and oxygen, relative to molybdenum, wherein $$0.1 \leq p \leq 0.6,$$

preferably $$0.2 \leq p \leq 0.4;$$

$$0.01 \leq q \leq 0.6,$$

preferably $$0.05 \leq q \leq 0.3;$$

$$0.01 \leq r \leq 0.6,$$

preferably $$0.03 \leq r \leq 0.3;$$

$$0 \leq s \leq 1,$$

preferably $$0 \leq s \leq 0.1;$$

and n is a number determined by the valence requirements of the other elements present, and that the compound oxide exhibits an X-ray diffraction pattern satisfying the following relationship (2):

$$0.40 \leq R \leq 0.75 \qquad (2)$$

wherein R represents the intensity ratio defined by the following formula (3):

$$R = P_1/(P_1 + P_2) \qquad (3)$$

wherein $P_1$ and $P_2$ represent the intensities of peak 1 and peak 2 appearing at diffraction angles (2θ) of 27.3±0.3° and 28.2±0.3°, respectively.

The XRD analysis of the ammoxidation catalyst of the present invention is conducted as follows.

In the XRD analysis of the ammoxidation catalyst, diffraction angles (2θ) are measured using Cu—Ka as a source of X-ray. The XRD analysis is conducted under the following conditions:

Tube voltage: 30 kV

Tube current: 40 mA

Divergence slit: 1°

Scatter slit: 1°

Receiving slit: 0.3 mm

Scanning speed: 6°/min.

Sampling interval: 0.02°.

In the XRD pattern obtained by the above-mentioned XRD analysis, the intensity ratio R is obtained as follows.

In the present invention, $P_1$ and $P_2$, which are the intensities of peak 1 and peak 2 appearing at diffraction angles (2θ) of 27.3±0.3° and 28.2±0.3°, respectively, can be obtained as follows. For example, in FIG. 2 hereof, which is an enlarged view of the XRD pattern of FIG. 1 (showing an XRD pattern of the ammoxidation catalyst obtained in Example 1), there is shown an explanatory view illustrating how to obtain the value of intensity ratio $R[=P_1/(P_1+P_2)]$. The explanatory view of FIG. 2 is taken in the range of from about 25° to about 29° in terms of the diffraction angle (2θ).

Figure 2:
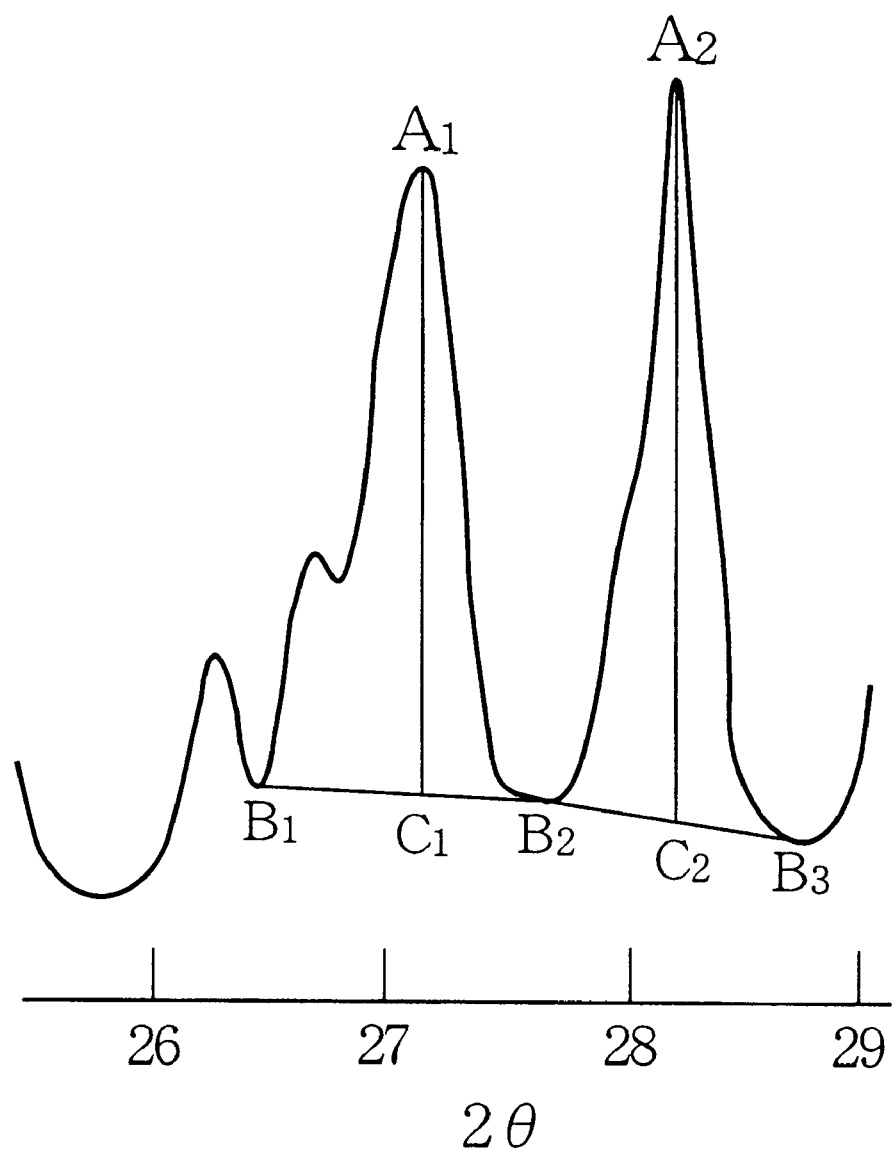
FIG. 2, which is an enlarged view of the XRD pattern of FIG. 1 and taken in the range of from about 25° to about 29° in terms of the diffraction angle (2θ), is an explanatory view showing how to obtain the value of intensity ratio R.

In FIG. 2, characters $A_1$ and $A_2$ designate the apexes of peaks 1 and 2 appearing at diffraction angles (2θ) of 27.3±0.3° and 28.2±0.3°, respectively. Characters $B_1$, $B_2$ and $B_3$ respectively designate points at which the curved line of the XRD pattern exhibits minimum values, as viewed along the intensity axis vertical to the 2θ-axis, in the ranges of 26.4±0.3°, 27.7±0.3° and 28.8±0.3°, respectively, in terms of the diffraction angle (2θ). In the present invention, the term "minimum value" used in connection with the curved line of the XRD pattern means a point at which the gradient of a tangential line of the curved line at a base portion of each of peaks 1 and 2 shifts from negative to positive, or a point at which the gradient converges to zero, wherein the gradient is taken as viewed in the coordinates of the 2θ-axis and the intensity axis. Character $C_1$ designates a point at which a line drawn downwardly from peak apex $A_1$ vertically to the 2θ-axis intersects with a straight line connecting points $B_1$ and $B_2$. Character $C_2$ designates a point at which a line drawn downwardly from peak apex $A_2$ vertically to the 2θ-axis intersects with a straight line connecting points $B_2$ and $B_3$.

The intensity of peak 1 (which is represented by character $P_1$ in the present invention) is defined as the length of straight line segment $A_1C_1$ which extends from peak apex $A_1$ (of peak 1) to point $C_1$; and the intensity of peak 2 (which is represented by character $P_2$ in the present invention) is defined as the length of straight line segment $A_2C_2$ which extends from peak apex $A_2$ (of peak 2) to point $C_2$.

Briefly stated, referring to FIG. 2 hereof showing an X-ray diffraction pattern taken in the range of from about 25° to about 29° in terms of the diffraction angle (2θ), the intensity of peak 1 is defined as the length of straight line segment $A_1C_1$ which extends from peak apex $A_1$ (of peak 1) to point $C_1$; and the intensity of peak 2 is defined as the length of straight line segment $A_2C_2$ which extends from peak apex $A_2$ (of peak 2) to point $C_2$, wherein:
the point $C_1$ is a point at which a line drawn downwardly from peak apex $A_1$ vertically to the 2θ-axis intersects with a straight line connecting points $B_1$ and $B_2$,
the point $C_2$ is a point at which a line drawn downwardly from peak apex $A_2$ vertically to the 2θ-axis intersects with a straight line connecting points $B_2$ and $B_3$, and
the points $B_1$, $B_2$ and $B_3$ are, respectively, points at which the curved line of the X-ray diffraction pattern exhibits minimum values, as viewed along the intensity axis vertical to the 2θ-axis, in the ranges of 26.4±0.3°, 27.7±0.3° and 28.8±0.3°, respectively, in terms of the diffraction angle (2θ).

As mentioned above, in the present invention, the intensity ratio (R) is defined as the ratio of the intensity of peak 1 to the sum of the intensities of peaks 1 and 2. Therefore, the intensity ratio R is defined by the following formula (3):

$$R=P_1/(P_1+P_2) \qquad (3)$$

wherein $P_1$ and $P_2$ represent the intensities of peak 1 and peak 2, respectively.

In the present invention, it is requisite that the intensity ratio R be in the range of from 0.40 to 0.75. It is preferred that the intensity ratio R is in the range of from 0.43 to 0.70, more advantageously from 0.50 to 0.69. When the intensity ratio R is less than 0.40 or is more than 0.75, problems arise in the ammoxidation of propane or isobutane using a catalyst exhibiting such a value of the intensity ratio R, not only in that, an extensive oxidative decomposition of feedstock ammonia occurs, but also in that the yield of acrylonitrile or methacrylonitrile is disadvantageously lowered.

The ammoxidation catalyst of the present invention may further comprise a silica carrier having supported thereon the compound oxide. The silica carrier is preferably present in an amount of from 20 to 60% by weight, more preferably from 20 to 40% by weight, based on the total weight of the compound oxide and the silica carrier.

With respect to the source of each component element for the ammoxidation catalyst of the present invention, there is no particular limitation. Representative examples of sources of component elements for the ammoxidation catalyst of the present invention include ammonium heptamolybdate $[(NH_4)_6Mo_7O_{24}.4H_2O]$ as a source of molybdenum; ammonium metavanadate $(NH_4VO_3)$ as a source of vanadium; telluric acid $(H_6TeO_6)$ as a source of tellurium; antimony trioxide $(Sb_2O_3)$ as a source of antimony; and niobic acid $(Nb_2O_5.nH_2O)$ as a source of niobium.

Examples of sources of other component elements for the ammoxidation catalyst of the present invention include nitrates, oxalates, acetates, hydroxides, oxides, ammonium salts and carbonates of elements, such as tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals.

With respect to the source of silica as an optionally employable carrier for the compound oxide of the ammoxidation catalyst of the present invention, a silica sol is preferred. Examples of silica sols include a silica sol stabilized with alkali metal ions and a silica sol stabilized with ammonium ions. A silica sol stabilized with ammonium ions is preferred.

The ammoxidation catalyst of the present invention can be produced by a conventional method. For example, the catalyst can be produced by a method comprising the steps of (1) preparing a raw material mixture (for example, a slurry of raw materials), (2) drying the raw material mixture obtained in step (1) above to obtain a dried catalyst precursor, and (3) subjecting the dried catalyst precursor obtained in step (2) above to calcination.

Hereinbelow, explanation is made with respect to a preferred embodiment of the above-mentioned method for producing the ammoxidation catalyst of the present invention, which comprises steps (1), (2) and (3), above.

In step (1), a raw material mixture is prepared. First, a solution is prepared by dissolving ammonium heptamolybdate, ammonium metavanadate and telluric acid in water (this solution is designated "solution A"). Alternatively, when antimony is used as a component element, a solution is first prepared by a method in which an antimony trioxide powder is dispersed in an aqueous solution of ammonium metavanadate, thereby obtaining a dispersion and the obtained dispersion is heated under reflux conditions to thereby obtain a solution or slurry, and then, ammonium heptamolybdate and, optionally, telluric acid are added to the obtained solution or slurry to obtain a further solution or slurry (this solution or slurry is designated "solution A'").

On the other hand, oxalic acid and niobic acid are dissolved in water or aqueous ammonia to obtain a solution (this solution is designated "solution B"). With respect to the obtained solution B, it is preferred that the molar ratio of oxalic acid to niobium is in the range of from 1 to 4, more advantageously from 2 to 4. With respect to the obtained solution B, it is also preferred that the molar ratio of ammonia to niobium is 2 or less, more advantageously 1 or less.

As mentioned above, the compound oxide of the catalyst of the present invention optionally contains at least one component element selected from the group consisting of the following elements: tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals. A nitrate, an oxalate, an acetate, a hydroxide, an oxide, an ammonium salt, a carbonate or the like of the above-mentioned at least one component element is dissolved in water, to obtain a solution or slurry (this solution or slurry is designated "solution C").

To solution A or A' are successively added solution B and solution C, to thereby obtain a raw material mixture.

When the ammoxidation catalyst of the present invention further comprises a silica carrier having supported thereon the compound oxide, the raw material mixture further contains a silica sol. The addition of a silica sol can be made at any time during the above preparation operation for the raw material mixture, which comprises preparing solution A or A' and solutions B and C and mixing together these solution A or A' and solutions B and C.

In step (2), the raw material mixture obtained in step (1) above is subjected to spray drying. The spray drying of the raw material mixture can be generally conducted by centrifugation, two-phase flow nozzle method or high pressure nozzle method to obtain a dried particulate catalyst precursor. In this instance, it is preferred to use air which has been heated by an electric heater, steam or the like, as a heat source for drying. It is preferred that the temperature of the spray dryer at an entrance to the dryer section thereof is from 150 to 300° C. Spray drying can be performed in an alternative handy way, for example, by spraying the raw material mixture onto a steel plate which has been heated to a temperature of 100 to 300° C.

In step (3), the dried particulate catalyst precursor obtained in step (2) above is calcined to thereby obtain a catalyst. The dried particulate catalyst precursor is calcined in an atmosphere of an inert gas, such as nitrogen gas, argon gas or helium gas, which is substantially free of oxygen, preferably under a flow of an inert gas, at a temperature of 500 to 700° C., preferably 550 to 650° C. for 0.5 to 5 hours, preferably 1 to 3 hours.

The oxygen concentration of the inert gas used for the calcination is generally 1,000 ppm or less, preferably 100 ppm or less, as measured by means of a gas chromatography or a trace oxygen analyzer.

For the calcination, use can be made of a kiln, such as a rotary kiln, a tunnel kiln, a muffle kiln and a fluidized firing kiln. The calcination of the catalyst can be repeatedly conducted.

Prior to and/or after the calcination in step (3), the dried catalyst precursor and/or a catalyst obtained by calcining the dried catalyst precursor may be subjected to pre-calcination or post-calcination. That is, prior to the calcination in step (3), the dried catalyst precursor obtained in step (2) above may be pre-calcined in an atmosphere of air or under a flow of air at a temperature of 200 to 350° C. for 10 minutes to 5 hours. Further, after the calcination, the obtained catalyst may be subjected to post-calcination in an atmosphere of air at a temperature of 200 to 400° C. for 5 minutes to 5 hours.

Further, after the calcination, the obtained catalyst may be subjected to grinding, and the resultant pulverized oxide catalyst may be subjected to recalcination in an atmosphere of an inert gas, such as nitrogen gas, argon gas or helium gas, which is substantially free of oxygen, preferably under a flow of an inert gas, at a temperature of 400 to 700° C., preferably 500 to 600° C. for 0.5 to 5 hours, preferably 1 to 3 hours.

Acrylonitrile or methacrylonitrile can be produced by the process of the present invention comprising reacting propane or isobutane with ammonia and molecular oxygen in the gaseous phase in the presence of the catalyst of the present invention.

Propane or isobutane and ammonia used in the process of the present invention need not be of a very high purity but may be of a commercial grade.

Examples of sources of molecular oxygen include air, oxygen-rich air, and pure oxygen. Further, such a source of molecular oxygen may be diluted with helium, argon, nitrogen, carbon dioxide, steam or the like.

In the process of the present invention, the molar ratio of ammonia to propane or isobutane used for the ammoxidation may be generally in the range of from 0.1 to 1.5, preferably from 0.2 to 1.2. By the use of the catalyst of the present invention, the ammoxidation of propane or isobutane can be conducted under conditions wherein the molar ratio of ammonia to propane or isobutane is at a low level, as compared to the level required in the case of a process using the conventional ammoxidation catalyst.

The molar ratio of molecular oxygen to propane or isobutane used for the ammoxidation may be generally in the range of from 0.2 to 6, preferably from 0.4 to 4.

In the process of the present invention, the ammoxidation temperature is generally in the range of from 350 to 600° C., preferably from 380 to 470° C.

In the process of the present invention, the ammoxidation pressure is generally in the range of from 0.1 to 10 atm., preferably from atmospheric pressure to 3 atm.

The time of contact (contact time) between the gaseous feedstocks and the catalyst is generally in the range of from 0.1 to 30 sec·g/cc, preferably from 0.5 to 10 sec·g/cc. In the process of the present invention, the contact time during the ammoxidation of propane or isobutane is determined according to the following formula:

$$\text{Contact time (sec} \cdot \text{g/cc)} = (W/F) \times 60 \times \frac{273}{(273+T)} \times P$$

wherein:

W represents the weight (g) of the catalyst contained in the reactor;

F represents the flow rate (cc/min) of the gaseous feedstocks [in terms of the value under the normal temperature and pressure conditions (0° C., 1 atm)];

T represents the ammoxidation temperature (° C.); and

P represents the ammoxidation pressure (atm.).

The process of the present invention for producing acrylonitrile or methacrylonitrile by ammoxidation of propane or isobutane in the gaseous phase can be conducted in a conventional reactor, such as a fixed-bed reactor, a fluidized-bed reactor or a moving-bed reactor. The reaction mode employed in the process of the present invention may be either a one-pass mode or a recycling mode.

BEST MODE FOR CARRYING OUT THE INVENTION

Hereinbelow, the present invention will be described in more detail with reference to the following Examples and Comparative Examples, which should not be construed as limiting the scope of the present invention.

In the following Examples and Comparative Examples, the conversion (%) of propane, the selectivity (%) for acrylonitrile, the yield (%) of acrylonitrile and the ammonia decomposition ratio (%), each used for evaluating the results of the ammoxidation of propane, are defined as follows:

$$\text{Conversion (\%) of propane} = \frac{\text{(mole of propane consumed)}}{\text{(mole of propane fed)}} \times 100$$

$$\text{Selectivity (\%) for acrylonitrile} = \frac{\text{(mole of acrylonitrile formed)}}{\text{(mole of propane consumed)}} \times 100$$

$$\text{Yield (\%) of acrylonitrile} = \frac{\text{(mole of acrylonitrile formed)}}{\text{(mole of propane fed)}} \times 100$$

$$\text{Ammonia decomposition ratio (\%)} = \frac{2 \times \text{(mole of nitrogen formed)}}{\text{(mole of ammonia fed)}} \times 100$$

EXAMPLE 1

Preparation of an ammoxidation catalyst

An ammoxidation catalyst comprising a compound oxide represented by the formula:

$$Mo_{1.0}V_{0.33}Nb_{0.11}Te_{0.22}O_n$$

was prepared as follows.

39.0 g of ammonium heptamolybdate [$(NH_4)_6Mo_7O_{24} \cdot 4H_2O$], 8.53 g of ammonium metavanadate ($NH_4VO_3$) and 11.16 g of telluric acid ($H_6TeO_6$) were dissolved in 160 g of water at a temperature of 60° C. while stirring, followed by cooling to 30° C., to thereby obtain a solution (solution A).

4.25 g of niobic acid ($Nb_2O_5 \cdot nH_2O$) ($Nb_2O_5$ content: 76.0% by weight) and 8.27 g of oxalic acid ($H_2C_2O_4 \cdot 2H_2O$) were dissolved in 50 g of water at a temperature of 60° C. while stirring, followed by cooling to 30° C., to thereby obtain a solution (solution B). In the obtained solution B, the molar ratio of oxalic acid to niobium (hereinafter, frequently referred to as "[$H_2C_2O_4$:Nb] molar ratio") was 2.7.

Solution B obtained above was added to solution A obtained above and the resultant mixture was stirred for about 30 minutes to obtain a raw material mixture.

The obtained raw material mixture was subjected to spray drying by spraying it onto a Teflon-coated iron plate heated to a temperature of 140° C., thereby obtaining a dried particulate catalyst precursor. 25 g of the obtained catalyst precursor was charged into a quartz tube having an inner diameter of 20 mm, and then calcined at a temperature of 600° C. for 2 hours under a stream of nitrogen gas at a flow rate of 1,000 Ncc/min. (Ncc means cc as measured under the normal temperature and pressure conditions, namely at 0° C. under 1 atm.), to thereby obtain a catalyst.

With respect to the oxygen concentration of the nitrogen gas used for the calcination, measurement was done by means of a trace oxygen analyzer 306WA (manufactured and sold by Teledyne Analytical Instruments, U.S.A.). As a result, it was found that the oxygen concentration of the nitrogen gas was 1 ppm.

The composition of the catalyst is shown in Table 1 together with the following conditions for the preparation of the catalyst: the [$H_2C_2O_4$:Nb] molar ratio and the [ammonia:Nb] molar ratio in solution B, the drying method for the raw material mixture, the calcination conditions, and whether or not a grinding of the catalyst was conducted.

X-ray diffractometry

An XRD pattern was obtained with respect to the catalyst obtained above. Specifically, the above obtained catalyst was subjected to measurement by X-ray diffractometry using an X-ray diffractometer RAD-IIIA (manufactured and sold by Rigaku Corporation, Japan) as follows.

Preparation of a sample

About 0.5 g of the catalyst was placed in an agate mortar and subjected to grinding for 2 minutes by manually operating an agate pestle. The resultant catalyst powder was subjected to sifting, to thereby obtain a powdery catalyst having a particle size of 53 μm or less. The obtained powdery catalyst was placed on a sample-holding table for an XRD pattern measurement. The table had a rectangular recess in the surface thereof (which has the following dimensions: a length of 20 mm, a width of 16 mm and a depth of 0.2 mm), and the powdery catalyst in the recess was pressed using a stainless steel spatula having a flat shape so that the surface of the powdery catalyst became flat.

XRD pattern measurement conditions

An XRD pattern measurement was conducted under the following conditions.

| | |
|---|---|
| Source of X-ray | $Cu-K\alpha_1 + Cu-K\alpha_2$ |
| Detector | Scintillation counter |
| Single crystal used for a monochromator | Graphite |
| Tube voltage | 30 kV |
| Tube current | 40 mA |
| Divergence slit | 1° |
| Scatter slit | 1° |
| Receiving slit | 0.3 mm |
| Scanning speed | 6°/min. |
| Sampling interval | 0.02° |
| Scanning method | 2θ/θ method |

The diffraction angle (2θ) correction was conducted by performing a calibration using X-ray diffractometry data obtained with respect to a silicon powder. As a smoothing treatment, both an 8-point high-frequency attenuation type smoothing and a 24-point differential type smoothing were performed. (A high-frequency amplification type smoothing was not performed.)

The XRD pattern obtained with respect to the catalyst in Example 1 is shown in FIG. 1, and the intensity ratio R determined with respect to peaks 1 and 2 [appearing at diffraction angles (2θ) of 27.3±0.3° and 28.2±0.3°, respectively] of the XRD pattern is shown in Table 1.

Ammoxidation of propane

Using the catalyst obtained above, an ammoxidation of propane was conducted as follows.

0.3 g of the obtained catalyst was charged into a fixed-bed reaction tube having an inner diameter of 4 mm. In the reaction tube containing the catalyst, an ammoxidation of propane was performed under conditions wherein the flow rate of a gaseous feedstock mixture (i.e., a gaseous mixture of propane, ammonia, molecular oxygen and helium) was 6 Ncc/min, the [propane:ammonia:molecular oxygen:helium] molar ratio in the gaseous feedstock mixture was 1.0:1.2:3.0:14.8, the ammoxidation temperature was 420° C., the ammoxidation pressure was 1 atm., and the contact time between the catalyst and the gaseous feedstock mixture was 1.2 sec·g/cc. The produced gaseous reaction mixture was subjected to analysis by means of an on-line gas chromatography.

The results of the evaluation of the above ammoxidation are shown in Table 3.

EXAMPLE 2
Preparation of an ammoxidation catalyst 2.0 g of the catalyst obtained in Example 1 above was charged into a quartz tube having an inner diameter of 20 mm, and then subjected to a re-calcination at 550° C. for 2 hours under a stream of nitrogen gas at a flow rate of 200 Ncc/min., to thereby obtain a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 3
Preparation of an ammoxidation catalyst 2.0 g of the catalyst obtained in Example 1 above was placed in an automatic agate mortar and subjected to grinding for 40 minutes. 1.5 g of the resultant powder was charged into a quartz tube having an inner diameter of 20 mm, and then subjected to a re-calcination at 550° C. for 2 hours under a stream of nitrogen gas at a flow rate of 200 Ncc/min., to thereby obtain a catalyst. The composition of the catalyst and the conditions for the preparation of the catalyst are shown in Table 1.

X-ray diffractometry

Figure 3:
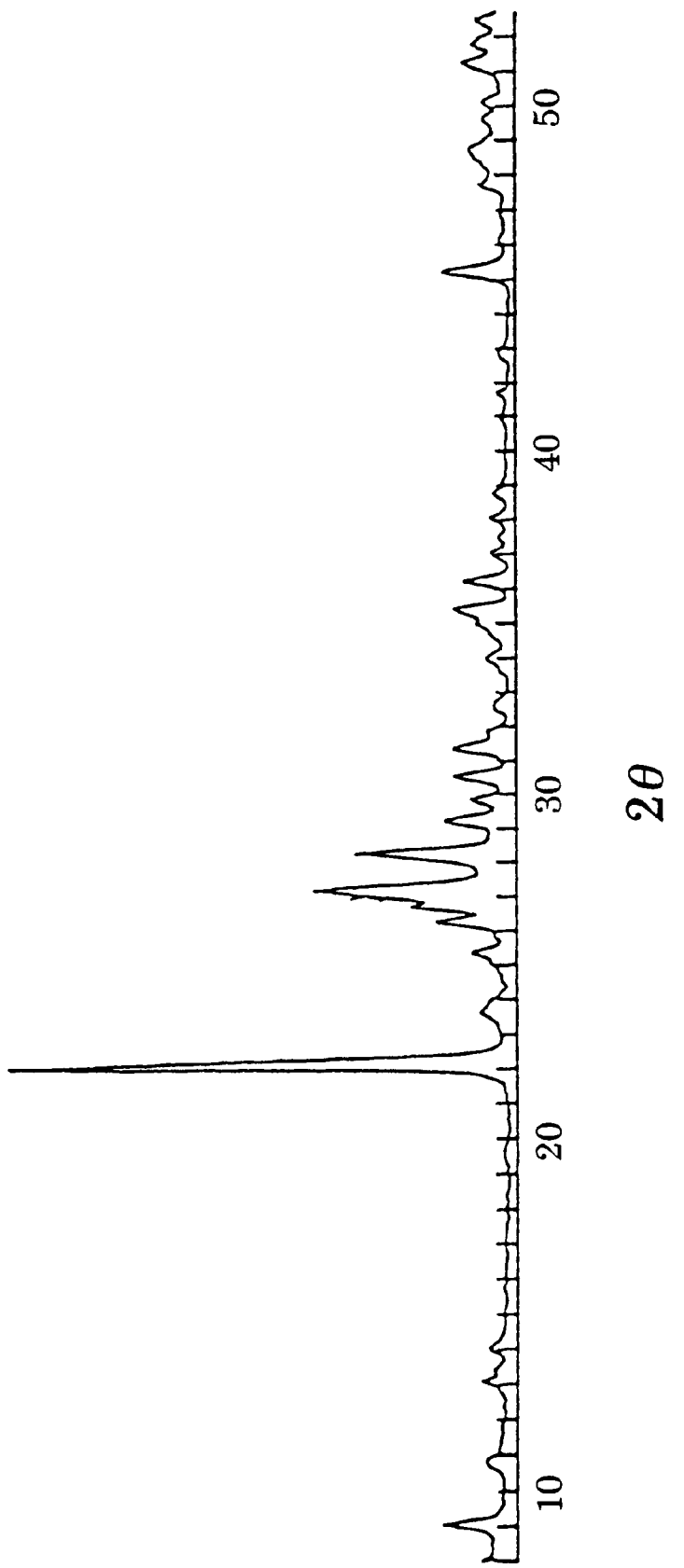
FIG. 3 is an XRD pattern of the ammoxidation catalyst obtained in Example 3.

With respect to the catalyst obtained above, substantially the same XRD pattern measurement as in Example 1 was repeated. The obtained XRD pattern is shown in FIG. 3, and the intensity ratio R is shown in Table 1.

Ammoxidation of propane

Substantially the same ammoxidation of propane as in Example 1 was repeated except that the catalyst obtained above was used (instead of the catalyst obtained in Example 1), that the flow rate of the gaseous feedstock mixture was 10 Ncc/min. (instead of 6 Ncc/min.) that the contact time was 0.5 sec·g/cc (instead of 1.2 sec-g/cc). The results of the evaluation of the above ammoxidation are shown in Table 3.

EXAMPLE 4
Preparation of an ammoxidation catalyst

A catalyst was prepared in substantially the same manner as in Example 3 except that the re-calcination was conducted for 1 hour (instead of 2 hours). The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 3 was repeated. The results of the evaluation of the above ammoxidation are shown in Table 3.

EXAMPLE 5
Preparation of an ammoxidation catalyst

An ammoxidation catalyst comprising a compound oxide represented by the formula:

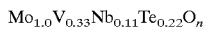

$$Mo_{1.0}V_{0.33}Nb_{0.11}Te_{0.22}O_n$$

was prepared as follows.

78.0 g of ammonium heptamolybdate [$(NH_4)_6Mo_7O_{24}.4H_2O$], 17.06 g of ammonium metavanadate ($NH_4VO_3$) and 22.3 g of telluric acid ($H_6TeO_6$) were dissolved in 350 g of water at a temperature of 70° C. while stirring, followed by cooling to 30° C., to thereby obtain a solution (solution A).

8.5 g of niobic acid ($Nb_2O_5.nH_2O$) ($Nb_2O_5$ content: 76.0% by weight) and 16.6 g of oxalic acid ($H_2C_2O_4.2H_2O$) were dissolved in 110 g of water at a temperature of 60° C. while stirring, followed by cooling to 30° C., to thereby obtain a solution (solution B). In the obtained solution B, the [$H_2C_2O_4$:Nb] molar ratio was 2.8.

Solution B obtained above was added to solution A obtained above and the resultant mixture was stirred for about 30 minutes to obtain a raw material mixture.

The obtained raw material mixture was subjected to spray drying by spraying it onto a Teflon-coated iron plate heated to a temperature of 140° C., thereby obtaining a dried particulate catalyst precursor.

Then, substantially the same calcination operation as in Example 1 was conducted except that 3 g of the catalyst precursor obtained above was used (instead of 25 g of the catalyst precursor obtained in Example 1), and that the flow rate of nitrogen gas was 330 Ncc/min. (instead of 1,000 Ncc/min.), to thereby obtain a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 6
Preparation of an ammoxidation catalyst

An ammoxidation catalyst comprising a compound oxide catalyst represented by the formula:

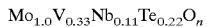

$$Mo_{1.0}V_{0.33}Nb_{0.11}Te_{0.22}O_n$$

was prepared as follows.

39.0 g of ammonium heptamolybdate [$(NH_4)_6Mo_7O_{24}.4H_2O$], 8.53 g of ammonium metavanadate ($NH_4VO_3$) and 11.16 g of telluric acid ($H_6TeO_6$) were dissolved in 160 g of water at a temperature of 60° C. while stirring, followed by cooling to 30° C., to thereby obtain a solution (solution A).

4.25 g of niobic acid ($Nb_2O_5.nH_2O$) ($Nb_2O_5$ content: 76.0% by weight) and 7.04 g of oxalic acid ($H_2C_2O_4.2H_2O$) were dissolved in 50 g of water at a temperature of 60° C. while stirring, followed by cooling to 30° C., to thereby obtain a solution (solution B). In the obtained solution B, the [$H_2C_2O_4$:Nb] molar ratio was 3.0.

Solution B obtained above was added to solution A obtained above and the resultant mixture was stirred for about 30 minutes to obtain a raw material mixture.

The obtained raw material mixture was subjected to spray drying by spraying it onto a Teflon-coated iron plate heated to a temperature of 140° C., thereby obtaining a dried particulate catalyst precursor.

Then, 10 g of the catalyst precursor obtained above was calcined in substantially the same manner as in Example 1, to thereby obtain a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 7

Preparation of an ammoxidation catalyst 1.0 g of the catalyst obtained in Example 6 above was placed in a porcelain dish and subjected to post-calcination at 320° C. for 0.3 hour in an atmosphere of air, thereby obtaining a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 8

Preparation of an ammoxidation catalyst 1.0 g of the catalyst obtained in Example 6 above was placed in a porcelain dish and subjected to post-calcination at 330° C. for 0.2 hour in an atmosphere of air, thereby obtaining a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 9

Preparation of an ammoxidation catalyst

A catalyst was prepared in substantially the same manner as in Example 1 except that, before the calcination, the catalyst precursor was pre-calcined at 250° C. for 1 hour in an atmosphere of air. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 10

Preparation of an ammoxidation catalyst

An ammoxidation catalyst comprising an compound oxide represented by the formula:

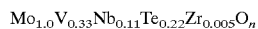

$$Mo_{1.0}V_{0.33}Nb_{0.11}Te_{0.22}Zr_{0.005}O_n$$

was prepared as follows.

The preparation of a catalyst was conducted in substantially the same manner as in Example 1 except that, after the mixing of solutions A and B, to the resultant mixture was added a dispersion obtained by dispersing 0.29 g of zirconyl nitrate [$ZrO(NO_3)_2 \cdot 2H_2O$] in 10.0 g of water. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 1

Preparation of an ammoxidation catalyst

A catalyst was prepared in substantially the same manner as in Example 1 except that 0.61 g of oxalic acid ($H_2C_2O_4 \cdot 2H_2O$) was used (instead of 8.27 g). In the obtained solution B, the [$H_2C_2O_4$:Nb] molar ratio was 0.2. The composition of the catalyst and the conditions for the preparation of the catalyst are shown in Table 1.

X-ray diffractometry

Figure 4:
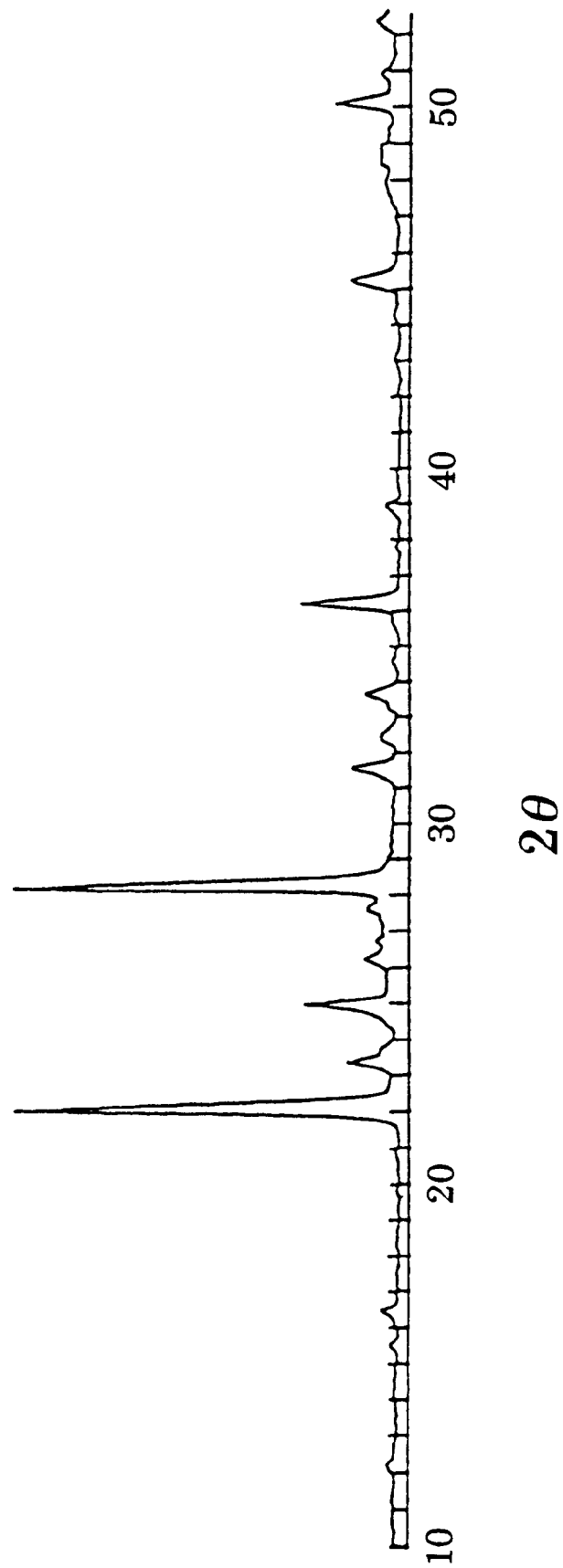
FIG. 4 is an XRD pattern of the ammoxidation catalyst obtained in Comparative Example 1.

With respect to the catalyst obtained above, substantially the same XRD pattern measurement as in Example 1 was repeated. The obtained XRD pattern is shown in FIG. 4, and the intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 2

Preparation of an ammoxidation catalyst

An ammoxidation catalyst comprising a compound oxide represented by the formula:

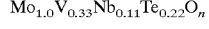

$$Mo_{1.0}V_{0.33}Nb_{0.11}Te_{0.22}O_n$$

was prepared as follows.

39.0 g of ammonium heptamolybdate [$(NH_4)_6Mo_7O_{24} \cdot 4H_2O$], 8.53 g of ammonium metavanadate ($NH_4VO_3$) and 11.16 g of telluric acid ($H_6TeO_6$) were dissolved in 160 g of water at a temperature of 60° C. while stirring, followed by cooling to 30° C., to thereby obtain a solution (solution A).

4.25 g of niobic acid ($Nb_2O_5 \cdot nH_2O$) ($Nb_2O_5$ content: 76.0% by weight) and 22.9 g of oxalic acid ($H_2C_2O_4 \cdot 2H_2O$) were dissolved in 50 g of water at a temperature of 60° C. while stirring, followed by cooling to 30° C., to thereby obtain a solution (solution B). In the obtained solution B, the [$H_2C_2O_4$:Nb] molar ratio was 7.5.

Solution B obtained above was added to solution A obtained above and the resultant mixture was stirred for about 30 minutes to obtain a raw material mixture.

The obtained raw material mixture was subjected to spray drying by spraying it onto a Teflon-coated iron plate heated to a temperature of 140° C., thereby obtaining a dried particulate catalyst precursor.

Then, 10 g of the obtained catalyst precursor was calcined in substantially the same manner as in Example 1, to thereby obtain a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. In the obtained XRD pattern, there was no peak appearing at a diffraction angle (2θ) of 27.3±0.3°.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 3

Preparation of an ammoxidation catalyst 6.0 g of the catalyst precursor obtained in Comparative Example 2 above was placed in a porcelain dish and pre-calcined at 250° C. for 2 hours in an atmosphere of air, thereby obtaining an oxide. 3 g of the obtained oxide was charged into a quartz tube having an inner diameter of 20 mm, and then calcined at 600° C. for 2 hours under a stream of nitrogen gas at a flow rate of 350 Ncc/min., to thereby obtain a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 4

Preparation of an ammoxidation catalyst

An ammoxidation catalyst comprising a compound oxide represented by the formula:

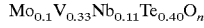

$Mo_{0.1}V_{0.33}Nb_{0.11}Te_{0.40}O_n$ was prepared as follows.

39.0 g of ammonium heptamolybdate [$(NH_4)_6Mo_7O_{24}\cdot 4H_2O$], 8.53 g of ammonium metavanadate ($NH_4VO_3$) and 20.30 g of telluric acid ($H_6TeO_6$) were dissolved in 160 g of water at a temperature of 60° C. while stirring, followed by cooling to 30° C., to thereby obtain a solution (solution A).

4.25 g of niobic acid ($Nb_2O_5\cdot nH_2O$) ($Nb_2O_5$ content: 76.0% by weight) and 22.9 g of oxalic acid ($H_2C_2O_4\cdot 2H_2O$) were dissolved in 50 g of water at a temperature of 60° C. while stirring, to thereby obtain a solution (solution B). In the obtained solution B, the [$H_2C_2O_4$:Nb] molar ratio was 7.5.

Solution B obtained above was added to solution A obtained above and the resultant mixture was stirred for about 30 minutes to obtain a raw material mixture.

The obtained raw material mixture was subjected to spray drying by spraying it onto a Teflon-coated iron plate heated to a temperature of 140° C., thereby obtaining a dried particulate catalyst precursor.

6.0 g of the catalyst precursor obtained was placed in a porcelain dish and pre-calcined at 250° C. for 2 hours in an atmosphere of air, thereby obtaining an oxide. 3 g of the obtained oxide was charged into a quartz tube having an inner diameter of 20 mm, and then calcined at 600° C. for 2 hours under a stream of nitrogen gas at a flow rate of 300 Ncc/min., to thereby obtain a catalyst. The composition of the catalyst and the conditions for the preparation of the catalyst are shown in Table 1.

X-ray diffractometry

Figure 5:
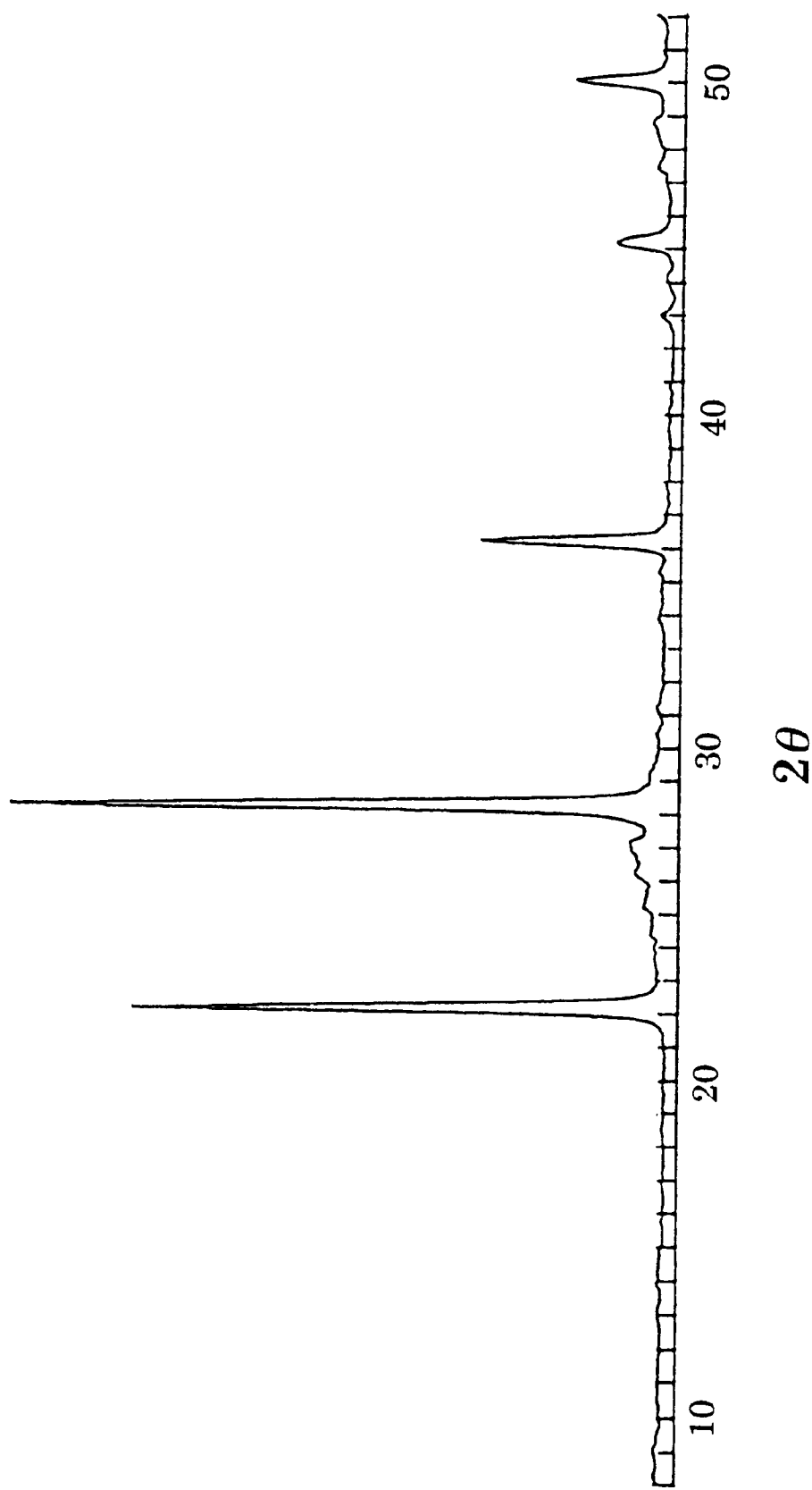
FIG. 5 is an XRD pattern of the ammoxidation catalyst obtained in Comparative Example 4.

With respect to the catalyst obtained above, substantially the same XRD pattern measurement as in Example 1 was repeated. The obtained XRD pattern is shown in FIG. 5, and the intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 5

Preparation of an ammoxidation catalyst 5.0 g of the catalyst precursor obtained in Example 1 above was placed in a porcelain dish and pre-calcined at 380° C. for 1 hour in an atmosphere of air, thereby obtaining an oxide. 2 g of the obtained oxide was charged into a quartz tube having an inner diameter of 20 mm, and then calcined at 600° C. for 2 hours under a stream of nitrogen gas at a flow rate of 200 Ncc/min., to thereby obtain a catalyst. The composition of the catalyst and the conditions for the preparation of the catalyst are shown in Table 1.

X-ray diffractometry

Figure 6:
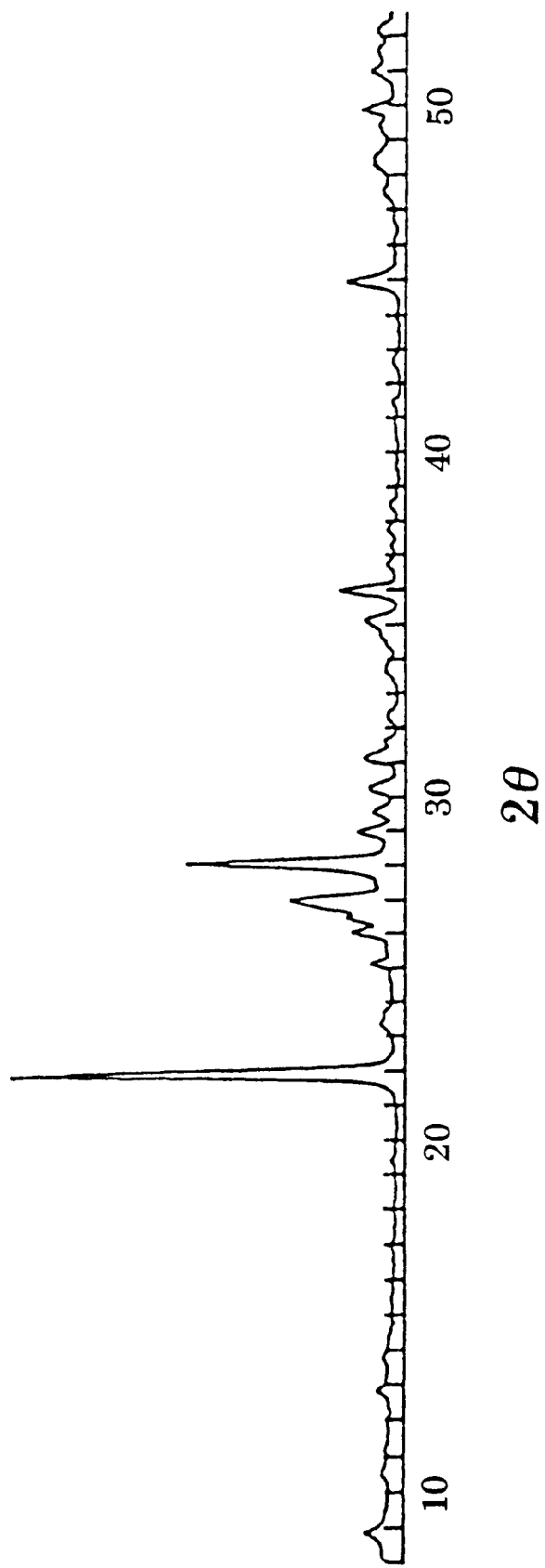
FIG. 6 is an XRD pattern of the ammoxidation catalyst obtained in Comparative Example 5.

With respect to the catalyst obtained above, substantially the same XRD pattern measurement as in Example 1 was repeated. The obtained XRD pattern is shown in FIG. 6, and the intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 6

Preparation of an ammoxidation catalyst 5.0 g of the catalyst precursor obtained in Example 1 above was placed in a porcelain dish and pre-calcined at 360° C. for 2 hours in an atmosphere of air, thereby obtaining an oxide. 2 g of the obtained oxide was charged into a quartz tube having an inner diameter of 20 mm, and then calcined at 600° C. for 2 hours under a stream of nitrogen gas at a flow rate of 200 Ncc/min., to thereby obtain a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 7

Preparation of an ammoxidation catalyst 1.0 g of the catalyst obtained in Example 1 above was placed in a porcelain dish and subjected to post-calcination at 450° C. for 2 hours in an atmosphere of air, thereby obtaining a catalyst. The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

COMPARATIVE EXAMPLE 8

Preparation of an ammoxidation catalyst

A catalyst was prepared in substantially the same manner as in Example 1 except that the calcination was conducted for 6 hours (instead of 2 hours). The composition of the catalyst and the conditions for the preparation of the catalyst are shown in Table 1.

X-ray diffractometry

With respect to the catalyst obtained above, substantially the same XRD pattern measurement as in Example 1 was repeated. The obtained intensity ratio R is shown in Table 1.

Ammoxidation of propane

Using the catalyst obtained above, substantially the same ammoxidation of propane as in Example 1 was repeated. The results of the evaluation of the above ammoxidation are shown in Table 3.

EXAMPLE 11

Preparation of an ammoxidation catalyst

An ammoxidation catalyst comprising a silica carrier having supported thereon a compound oxide, wherein the silica carrier is present in an amount of 30% by weight, based on the total weight of the compound oxide and the silica carrier, and wherein the compound oxide is represented by the formula:

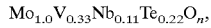

$Mo_{1.0}V_{0.33}Nb_{0.11}Te_{0.22}O_n$, was prepared as follows.

164.31 g of ammonium heptamolybdate [$(NH_4)_6Mo_7O_{24} \cdot 4H_2O$], 36.05 g of ammonium metavanadate ($NH_4VO_3$) and 47.15 g of telluric acid ($H_6TeO_6$) were dissolved in 720 g of water at a temperature of 60° C. while stirring, to thereby obtain a solution (solution A).

17.64 g of niobic acid ($Nb_2O_5 \cdot nH_2O$) ($Nb_2O_5$ content: 76.6% by weight) and 38.45 g of oxalic acid ($H_2C_2O_4 \cdot 2H_2O$) were dissolved in 170 g of water at a temperature of 60° C. while stirring, followed by cooling to 30° C., to thereby obtain a solution (solution B). In the obtained solution B, the [$H_2C_2O_4$:Nb] molar ratio was 3.0.

To solution A obtained above was added 300 g of a silica sol having an $SiO_2$ content of 30 wt % while stirring, and the resultant mixture was then cooled to 30° C., followed by addition of solution B obtained above, to thereby obtain a raw material mixture.

The obtained raw material mixture was subjected to spray drying using a centrifugation type spray-drying apparatus under conditions wherein the inlet temperature of the apparatus was 240° C. and the outlet temperature of the apparatus was 145° C., to obtain a dried particulate catalyst precursor.

The obtained catalyst precursor was pre-calcined at 275° C. for 2 hours in an atmosphere of air, to obtain an oxide. 80 g of the obtained oxide was charged into a stainless steel tube having an inner diameter of 1 inch, and then calcined at a temperature of 600° C. for 2 hours under a stream of nitrogen gas at a flow rate of 150 Ncc/min, to thereby obtain a catalyst. The composition of the catalyst and the conditions for the preparation of the catalyst are shown in Table 2.

X-ray diffractometry

Figure 7:
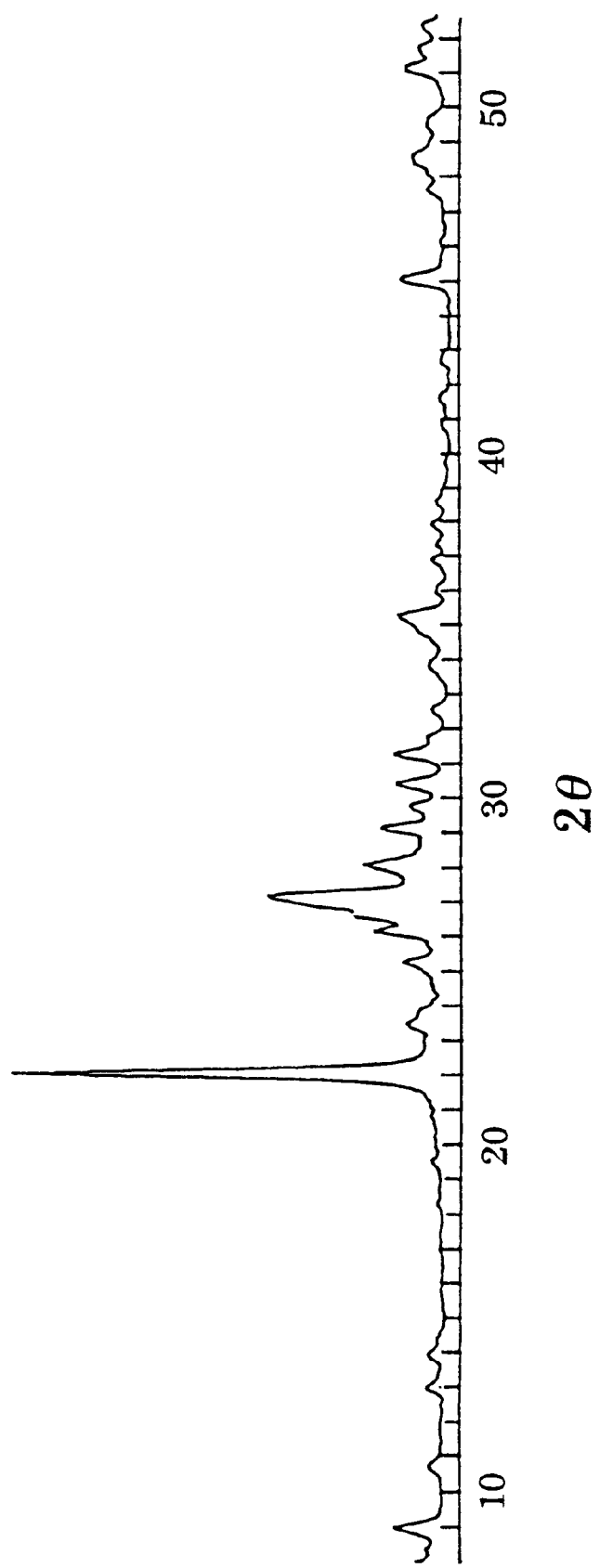
FIG. 7 is an XRD pattern of the ammoxidation catalyst obtained in Example 11.

With respect to the catalyst obtained above, substantially the same XRD pattern measurement as in Example 1 was repeated. The obtained XRD pattern is shown in FIG. 7, and the intensity ratio R is shown in Table 2.

Ammoxidation of propane

Using the catalyst obtained above, an ammoxidation of propane was conducted as follows.

45 g of the obtained catalyst was charged into a Vycor glass fluidized-bed reactor having an inner diameter of 25 mm. In the reactor containing the catalyst, an ammoxidation of propane was performed under conditions wherein the flow rate of a gaseous feedstock mixture (i.e., a gaseous mixture of propane, ammonia, molecular oxygen and helium) was 350 Ncc/min, the [propane:ammonia:molecular oxygen:helium] molar ratio in the gaseous feedstock mixture was 1.0:1.2:3.0:12.0, the ammoxidation temperature was 430° C., the ammoxidation pressure was 1 atm., and the contact time between the catalyst and the gaseous feedstock mixture was 3.0 sec·g/cc. The produced gaseous reaction mixture was subjected to analysis by means of an on-line chromatography.

The results of the evaluation of the above ammoxidation are shown in Table 4.

EXAMPLE 12

Preparation of an ammoxidation catalyst

A catalyst was prepared in substantially the same manner as in Example 11 except that, in the preparation of solution B, 34.60 g of oxalic acid ($H_2C_2O_4 \cdot 2H_2O$) was used (instead of 38.45 g). In the obtained solution B, the [$H_2C_2O_4$:Nb] molar ratio was 2.7. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

EXAMPLE 13

Preparation of an ammoxidation catalyst

A catalyst was prepared in substantially the same manner as in Example 11 except that, in the preparation of solution B, 44.85 g of oxalic acid ($H_2C_2O_4 \cdot 2H_2O$) was used (instead of 38.45 g). In the obtained solution B, the [$H_2C_2O_4$:Nb] molar ratio was 3.5. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

EXAMPLE 14

Preparation of an ammoxidation catalyst

A catalyst was prepared in substantially the same manner as in Example 11 except that, in the preparation of solution B, 160 g of water was used (instead of 170 g) and 6.9 g of 25 wt % aqueous ammonia was added. In the obtained solution B, the [$H_2C_2O_4$:Nb] molar ratio was 3.0 and the [ammonia:Nb] molar ratio was 1.0. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

COMPARATIVE EXAMPLE 9

Preparation of an ammoxidation catalyst

A catalyst was prepared in substantially the same manner as in Example 11 except that, in the preparation of solution B, 150 g of water was used (instead of 170 g) and 16.6 g of 25 wt % aqueous ammonia was added. In the obtained solution B, the [$H_2C_2O_4$:Nb] molar ratio was 3.0 and the [ammonia:Nb] molar ratio was 2.4. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

COMPARATIVE EXAMPLE 10

Preparation of an ammoxidation catalyst

A catalyst was prepared in substantially the same manner as in Example 11 except that, in the preparation of solution B, 96.11 g of oxalic acid ($H_2C_2O_4 \cdot 2H_2O$) was used (instead of 38.45 g). In the obtained solution B, the [$H_2C_2O_4$:Nb] molar ratio was 7.5. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

COMPARATIVE EXAMPLE 11

Preparation of an ammoxidation catalyst

A catalyst was prepared in substantially the same manner as in Example 11 except that, in the preparation of solution B, 3.84 g of oxalic acid ($H_2C_2O_4 \cdot 2H_2O$) was used (instead of 38.45 g). In the obtained solution B, the [$H_2C_2O_4$:Nb] molar ratio was 0.3. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

COMPARATIVE EXAMPLE 12

Preparation of an ammoxidation catalyst 45.0 g of the catalyst obtained in Example 11 above was placed in a porcelain dish and subjected to post-calcination at 450° C. for 2 hours in an atmosphere of air, thereby obtaining a catalyst. The composition of the catalyst and the conditions for the preparation of the catalyst are shown in Table 2.

X-ray diffractometry

With respect to the catalyst obtained above, substantially the same XRD pattern measurement as in Example 1 was repeated. The obtained XRD pattern is shown in FIG. 8, and the intensity ratio R is shown in Table 2.

Ammoxidation of propane

Using the catalyst obtained above, substantially the same ammoxidation of propane as in Example 11 was repeated. The results of the evaluation of the above ammoxidation are shown in Table 4.

TABLE 1

| | Composition of ammoxidation catalyst | Molar ratio to Nb[1] $H_2C_2O_4$ | Ammonia | Pre-calcination Temp. (° C.) | Time (hr) | Calcination Temp. (° C.) | Time (hr) | Grinding | Re-calcination Temp. (° C.) | Time (hr) | Post-calcination Temp. (° C.) | Time (hr) | Intensity ratio R[2] |
|---|---|---|---|---|---|---|---|---|---|---|---|---|---|
| Ex. 1 | $Mo_{1.0}V_{0.33}Nb_{0.11}Te_{0.22}O_n$ | 2.7 | 0 | — | — | 600 | 2 | no | — | — | — | — | 0.46 |
| Ex. 2 | $Mo_{1.0}V_{0.33}Nb_{0.11}Te_{0.22}O_n$ | 2.7 | 0 | — | — | 600 | 2 | no | 550 | 2 | — | — | 0.47 |
| Ex. 3 | $Mo_{1.0}V_{0.33}Nb_{0.11}Te_{0.22}O_n$ | 2.7 | 0 | — | — | 600 | 2 | 40 min. | 550 | 2 | — | — | 0.56 |
| Ex. 4 | $Mo_{1.0}V_{0.33}Nb_{0.11}Te_{0.22}O_n$ | 2.7 | 0 | — | — | 600 | 2 | 40 min. | 550 | 1 | — | — | 0.55 |
| Ex. 5 | $Mo_{1.0}V_{0.33}Nb_{0.11}Te_{0.22}O_n$ | 2.8 | 0 | — | — | 600 | 2 | no | — | — | — | — | 0.45 |
| Ex. 6 | $Mo_{1.0}V_{0.33}Nb_{0.11}Te_{0.22}O_n$ | 3.0 | 0 | — | — | 600 | 2 | no | — | — | — | — | 0.46 |
| Ex. 7 | $Mo_{1.0}V_{0.33}Nb_{0.11}Te_{0.22}O_n$ | 3.0 | 0 | — | — | 600 | 2 | no | — | — | 320 | 0.3 | 0.48 |
| Ex. 8 | $Mo_{1.0}V_{0.33}Nb_{0.11}Te_{0.22}O_n$ | 3.0 | 0 | — | — | 600 | 2 | no | — | — | 330 | 0.2 | 0.48 |
| Ex. 9 | $Mo_{1.0}V_{0.33}Nb_{0.11}Te_{0.22}O_n$ | 2.7 | 0 | 250 | 1 | 600 | 2 | no | — | — | — | — | 0.45 |
| Ex. 10 | $Mo_{1.0}V_{0.33}Nb_{0.11}Te_{0.22}Zr_{0.005}O_n$ | 2.7 | 0 | — | — | 600 | 2 | no | — | — | — | — | 0.49 |
| Comp. Ex. 1 | $Mo_{1.0}V_{0.33}Nb_{0.11}Te_{0.22}O_n$ | 0.2 | 0 | — | — | 600 | 2 | no | — | — | — | — | 0.01 |
| Comp. Ex. 2 | $Mo_{1.0}V_{0.33}Nb_{0.11}Te_{0.22}O_n$ | 7.5 | 0 | — | — | 600 | 2 | no | — | — | — | — | 0 |
| Comp. | $Mo_{1.0}V_{0.33}Nb_{0.11}Te_{0.22}O_n$ | 7.5 | 0 | 250 | 2 | 600 | 2 | no | — | — | — | — | 0.20 |

TABLE 1-continued

| | Composition of ammoxidation catalyst | Molar ratio to Nb[1] $H_2C_2O_4$ | Molar ratio to Nb[1] Ammonia | Pre-calcination Temp. (°C.) | Pre-calcination Time (hr) | Calcination Temp. (°C.) | Calcination Time (hr) | Grind-ing | Re-calcination Temp. (°C.) | Re-calcination Time (hr) | Post-calcination Temp. (°C.) | Post-calcination Time (hr) | Intensity ratio R[2] |
|---|---|---|---|---|---|---|---|---|---|---|---|---|---|
| Ex. 3 Comp. Ex. 4 | $Mo_{1.0}V_{0.33}Nb_{0.11}Te_{0.40}O_n$ | 7.5 | 0 | 250 | 2 | 600 | 2 | no | — | — | — | — | 0.02 |
| Comp. Ex. 5 | $Mo_{1.0}V_{0.33}Nb_{0.11}Te_{0.22}O_n$ | 2.7 | 0 | 380 | 1 | 600 | 2 | no | — | — | — | — | 0.32 |
| Comp. Ex. 6 | $Mo_{1.0}V_{0.33}Nb_{0.11}Te_{0.22}O_n$ | 2.7 | 0 | 360 | 2 | 600 | 2 | no | — | — | — | — | 0.18 |
| Comp. Ex. 7 | $Mo_{1.0}V_{0.33}Nb_{0.11}Te_{0.22}O_n$ | 2.7 | 0 | — | — | 600 | 2 | no | — | — | 450 | 2 | 0.88 |
| Comp. Ex. 8 | $Mo_{1.0}V_{0.33}Nb_{0.11}Te_{0.22}O_n$ | 2.7 | 0 | — | — | 600 | 6 | no | — | — | — | — | 0.82 |

Note [1]: Molar ratio of oxalic acid ($H_2C_2O_4$) to niobium (Nb); and molar ratio of ammonia to niobium (Nb).
Note [2]: Intensity ratio R means the intensity ratio defined by the formula: $R = P_1/(P_1 + P_2)$ wherein $P_1$ and $P_2$ represent the intensities of peaks 1 and 2 appearing at diffraction angles (2θ) of 27.3° ± 0.3° and 28.2° ± 0.3°, respectively.

TABLE 2

| | Composition of ammoxidation catalyst[3] | Molar ratio to Nb[1] $H_2C_2O_4$ | Molar ratio to Nb[1] Ammonia | Pre-calcination Temp. (°C.) | Pre-calcination Time (hr) | Calcination Temp. (°C.) | Calcination Time (hr) | Grind-ing | Re-calcination Temp. (°C.) | Re-calcination Time (hr) | Post-calcination Temp. (°C.) | Post-calcination Time (hr) | Intensity ratio R[2] |
|---|---|---|---|---|---|---|---|---|---|---|---|---|---|
| Ex. 11 | $Mo_{1.0}V_{0.33}Nb_{0.11}Te_{0.22}O_nSiO_2$ | 3.0 | 0 | 275 | 2 | 600 | 2 | no | — | — | — | — | 0.69 |
| Ex. 11 | $Mo_{1.0}V_{0.33}Nb_{0.11}Te_{0.22}O_nSiO_2$ | 3.0 | 0 | 275 | 2 | 600 | 2 | no | — | — | — | — | 0.69 |
| Ex. 12 | $Mo_{1.0}V_{0.33}Nb_{0.11}Te_{0.22}O_nSiO_2$ | 2.7 | 0 | 275 | 2 | 600 | 2 | no | — | — | — | — | 0.49 |
| Ex. 13 | $Mo_{1.0}V_{0.33}Nb_{0.11}Te_{0.22}O_nSiO_2$ | 3.5 | 0 | 275 | 2 | 600 | 2 | no | — | — | — | — | 0.64 |
| Ex. 14 | $Mo_{1.0}V_{0.33}Nb_{0.11}Te_{0.22}O_nSiO_2$ | 3.0 | 1.0 | 275 | 2 | 600 | 2 | no | — | — | — | — | 0.55 |
| Comp. Ex. 9 | $Mo_{1.0}V_{0.33}Nb_{0.11}Te_{0.22}O_nSiO_2$ | 3.0 | 2.4 | 275 | 2 | 600 | 2 | no | — | — | — | — | 0.16 |
| Comp. Ex. 10 | $Mo_{1.0}V_{0.33}Nb_{0.11}Te_{0.22}O_nSiO_2$ | 7.5 | 0 | 275 | 2 | 600 | 2 | no | — | — | — | — | 0.32 |
| Comp. Ex. 11 | $Mo_{1.0}V_{0.33}Nb_{0.11}Te_{0.22}O_nSiO_2$ | 0.3 | 0 | 275 | 2 | 600 | 2 | no | — | — | — | — | 0.02 |
| Comp. Ex. 12 | $Mo_{1.0}V_{0.33}Nb_{0.11}Te_{0.22}O_nSiO_2$ | 3.0 | 0 | 275 | 2 | 600 | 2 | no | — | — | 450 | 2 | 0.87 |

Note [1]: Molar ratio of oxalic acid ($H_2C_2O_4$) to niobium (Nb); and molar ratio of ammonia to niobium (Nb).
Note [2]: Intensity ratio R means the intensity ratio defined by the formula: $R = P_1/(P_1 + P_2)$ wherein $P_1$ and $P_2$ represent the intensities of peaks 1 and 2 appearing at diffraction angles (2θ) of 27.3° ± 0.3° and 28.2° ± 0.3°, respectively.
Note [3]: In Examples 11 to 14 and Comparative Examples 9 to 12, the amount of the silica carrier ($SiO_2$) is 30 wt %.

TABLE 3

| | Ammoxidation conditions [propane:ammonia:molecular oxygen:helium] molar ratio | Ammoxidation conditions Reaction temperature (°C.) | Ammoxidation conditions Contact time (sec · g/cc) | Evaluation of ammoxidation Ammonia decomposition ratio (%) | Evaluation of ammoxidation Conversion of propane (%) | Evaluation of ammoxidation Selectivity of acrylonitrile (%) | Evaluation of ammoxidation Yield of acrylonitrile (%) |
|---|---|---|---|---|---|---|---|
| Ex. 1 | 1.0/1.2/3.0/14.8 | 420 | 1.2 | 32.1 | 90.8 | 61.8 | 56.1 |
| Ex. 2 | 1.0/1.2/3.0/14.8 | 420 | 1.2 | 32.8 | 91.5 | 61.3 | 56.1 |
| Ex. 3 | 1.0/1.2/3.0/14.8 | 420 | 0.5 | 30.5 | 92.9 | 63.5 | 58.9 |
| Ex. 4 | 1.0/1.2/3.0/14.8 | 420 | 0.5 | 29.4 | 93.1 | 63.3 | 58.9 |
| Ex. 5 | 1.0/1.2/3.0/14.8 | 420 | 1.2 | 31.0 | 90.4 | 61.2 | 55.4 |
| Ex. 6 | 1.0/1.2/3.0/14.8 | 420 | 1.2 | 33.1 | 89.7 | 60.2 | 54.0 |
| Ex. 7 | 1.0/1.2/3.0/14.8 | 420 | 1.2 | 32.2 | 90.5 | 61.2 | 55.4 |
| Ex. 8 | 1.0/1.2/3.0/14.8 | 420 | 1.2 | 31.8 | 90.6 | 61.6 | 55.6 |
| Ex. 9 | 1.0/1.2/3.0/14.8 | 420 | 1.2 | 33.1 | 89.2 | 61.9 | 55.2 |
| Ex. 10 | 1.0/1.2/3.0/14.8 | 420 | 1.2 | 30.7 | 90.6 | 61.7 | 55.9 |
| Comp. Ex. 1 | 1.0/1.2/3.0/14.8 | 420 | 1.2 | 96.6 | 1.4 | 37.1 | 0.5 |
| Comp. Ex. 2 | 1.0/1.2/3.0/14.8 | 420 | 1.2 | 93.3 | 10.3 | 40.9 | 4.2 |
| Comp. Ex. 3 | 1.0/1.2/3.0/14.8 | 420 | 1.2 | 61.2 | 66.1 | 66.2 | 43.4 |
| Comp. Ex. 4 | 1.0/1.2/3.0/14.8 | 420 | 1.2 | 97.5 | 7.4 | 36.9 | 2.7 |
| Comp. Ex. 5 | 1.0/1.2/3.0/14.8 | 420 | 1.2 | 40.0 | 86.5 | 59.7 | 51.6 |
| Comp. Ex. 6 | 1.0/1.2/3.0/14.8 | 420 | 1.2 | 59.7 | 41.7 | 58.9 | 24.6 |

TABLE 3-continued

| | Ammoxidation conditions | | | Evaluation of ammoxidation | | | |
|---|---|---|---|---|---|---|---|
| | [propane:ammonia:molecular oxygen:helium] molar ratio | Reaction temperature (° C.) | Contact time (sec · g/cc) | Ammonia decomposition ratio (%) | Conversion of propane (%) | Selectivity of acrylonitrile (%) | Yield of acrylonitrile (%) |
| Comp. Ex. 7 | 1.0/1.2/3.0/14.8 | 420 | 1.2 | 80.4 | 35.5 | 59.3 | 21.0 |
| Comp. Ex. 8 | 1.0/1.2/3.0/14.8 | 420 | 1.2 | 79.1 | 30.5 | 63.9 | 19.5 |

TABLE 4

| | Ammoxidation conditions | | | Evaluation of ammoxidation | | | |
|---|---|---|---|---|---|---|---|
| | [propane:ammonia:molecular oxygen:helium] molar ratio | Reaction temperature (° C.) | Contact time (sec · g/cc) | Ammonia decomposition ratio (%) | Conversion of propane (%) | Selectivity of acrylonitrile (%) | Yield of acrylonitrile (%) |
| Ex. 11 | 1.0/1.2/3.0/12.0 | 430 | 3.0 | 31.6 | 85.2 | 60.9 | 51.9 |
| Ex. 12 | 1.0/1.2/3.0/12.0 | 430 | 3.0 | 31.4 | 84.0 | 57.0 | 47.9 |
| Ex. 13 | 1.0/1.2/3.0/12.0 | 430 | 3.0 | 31.3 | 84.9 | 60.1 | 51.0 |
| Ex. 14 | 1.0/1.2/3.0/12.0 | 430 | 3.0 | 31.5 | 85.0 | 59.0 | 50.2 |
| Comp. Ex. 9 | 1.0/1.2/3.0/12.0 | 430 | 3.0 | 61.2 | 72.8 | 46.6 | 33.9 |
| Comp. Ex. 10 | 1.0/1.2/3.0/12.0 | 430 | 3.0 | 47.7 | 74.1 | 52.8 | 39.1 |
| Comp. Ex. 11 | 1.0/1.2/3.0/12.0 | 430 | 3.0 | 95.8 | 1.2 | 31.2 | 0.4 |
| Comp. Ex. 12 | 1.0/1.2/3.0/12.0 | 430 | 3.0 | 63.5 | 44.1 | 56.7 | 25.0 |

INDUSTRIAL APPLICABILITY

By the use of the ammoxidation catalyst of the present invention in producing acrylonitrile or methacrylonitrile from propane or isobutane, not only can acrylonitrile or methacrylonitrile be produced in high yield, but also oxidative decomposition of ammonia feedstock into nitrogen can be effectively suppressed, thereby enabling an improved utilization of ammonia as a feedstock.

What is claimed is:

1. An ammoxidation catalyst for use in producing acrylonitrile or methacrylonitrile from propane or isobutane by ammoxidation in the gaseous phase, comprising a compound oxide represented by the following formula (1):

$$Mo_{1.0}V_pX_qNb_rZ_sO_n \quad (1)$$

wherein:

X is at least one element selected from the group consisting of tellurium and antimony;

Z is at least one element selected from the group consisting of tantalum, tungsten, chromium, titanium, zirconium, bismuth, tin, hafnium, manganese, rhenium, iron, ruthenium, cobalt, rhodium, nickel, palladium, platinum, silver, zinc, boron, aluminum, gallium, indium, germanium, lead, phosphorus, rare earth elements and alkaline earth metals, and p, q, r, s and n are, respectively, the atomic ratios of vanadium, X, niobium, Z and oxygen, relative to molybdenum, wherein $0.1 \leq p \leq 0.6$;

$0.01 \leq q \leq 0.6$;

$0.01 \leq r \leq 0.6$;

$0 \leq s \leq 1$;

and n is a number determined by the valence requirements of the other elements present, said compound oxide exhibiting an X-ray diffraction pattern satisfying the following relationship (2):

$$0.40 \leq R \leq 0.75 \quad (2)$$

wherein R represents the intensity ratio defined by the following formula (3):

$$R = P_1/(P_1+P_2) \quad (3)$$

wherein $P_1$ and $P_2$ represent the intensities of peak 1 and peak 2 appearing at diffraction angles (2θ) of 27.3±0.3° and 28.2±0.3°, respectively.

2. The catalyst according to claim 1, wherein R in relationship (2) satisfies the following relationship:

$$0.43 \leq R \leq 0.70.$$

3. The catalyst according to claim 2, which further comprises a silica carrier having supported thereon said compound oxide, wherein said silica carrier is present in an amount of from 20 to 60% by weight, based on the total weight of said compound oxide and said silica carrier.

4. The catalyst according to claim 1, which further comprises a silica carrier having supported thereon said compound oxide, wherein said silica carrier is present in an amount of from 20 to 60% by weight, based on the total weight of said compound oxide and said silica carrier.

* * * * *